United States Patent [19]

Stewart

[11] Patent Number: 4,764,307
[45] Date of Patent: Aug. 16, 1988

[54] PREPARATION OF SURFACTANTS

[75] Inventor: Nevin J. Stewart, Guildford, England

[73] Assignee: The British Petroleum Company p.l.c., London, England

[21] Appl. No.: 871,478

[22] Filed: Jun. 6, 1986

[30] Foreign Application Priority Data

Jun. 15, 1985 [GB] United Kingdom ................ 8515225

[51] Int. Cl.$^4$ .................. C07C 143/11; C07C 143/38
[52] U.S. Cl. .............................. 260/512 R; 260/513 B
[58] Field of Search ........................ 260/512 R, 513 B

[56] References Cited

U.S. PATENT DOCUMENTS 2,115,192  4/1938  Bruson ........................... 260/512 R
3,275,682  9/1966  Bakker et al. .................... 260/513 B
4,267,123  5/1981  Chen et al. ..................... 260/501.12
4,442,042  4/1984  Schmitt .......................... 260/512 R
4,600,516  7/1986  Wester et al. ................... 260/512 R Primary Examiner—Nicky Chan
Attorney, Agent, or Firm—Morgan & Finnegan

[57] ABSTRACT

Alkyl-, aryl-, or alkylaryl-alkoxy ethane sulphonates are prepared by reacting the corresponding halides with potassium or ammonium sulphite in the presence of water in amount less than 50% by weight of the alkoxy ethane halide.

Reducing the water content of the reaction mixture to a low level increases the throughput and yield and reduces the increase in viscosity of the reaction mixture as the reaction proceeds.

10 Claims, No Drawings

PREPARATION OF SURFACTANTS

This invention relates to a process for the preparation of alkyl-, aryl- or alkylaryl-alkoxy ethane sulphonates, suitable for use as surfactants.

Numerous attempts have been made to develop surfactant compositions for use in enhanced oil recovery and the patent literature is replete with descriptions of formulations, see for example, U.S. Pat. Nos. 4,424,135, 4,159,037, 4,110,228, 4,066,124 and 4,018,278.

A useful summary of the art is given in Kirk-Othmer's Encyclopedia of Chemical Technology, Third Edition, Volume 17, pages 168-182. This indicates that most compositions contain (a) a main surfactant which is either a petroleum or a synthetic hydrocarbyl sulphonate and (b) co-surfactants which include simple alcohols, ethoxylated alcohols and sulphated ethoxylated alcohols.

It has also been disclosed that alkyl and alkylaryl polyalkoxy ethane sulphonates may be used as co-surfactants. These compounds are generally prepared by a three-stage process. In the first stage of a typical process an alcohol or alkyl phenol is condensed with an alkylene oxide in the presence of sodium or potassium hydroxide to form an alkoxy alcohol. This is then halogenated by treatment with thionyl or sulphuryl chloride, usually in the absence of a catalyst. Finally the halide is converted to a sulphonate by reaction with aqueous sodium sulphite, again, usually in the absence of a catalyst.

The sulphonation reaction is described in U.S. Pat. No. 2,115,192. The reaction takes place in an aqueous medium which is generally about 70% by weight of the total reaction mixture, the weight ratio of water to ethane chloride being in the range 3 to 4:1. Generally continuous agitation is necessary to maintain the rate of reaction.

It has been found that in such reactions the reaction mixture may become viscous and, as the viscosity increases, agitation of the reaction mixture becomes difficult, heat transfer is reduced and control of the reaction becomes difficult.

We have now discovered that employing potassium or ammonium sulphite as the sulphonate source and reducing the water content to a low level increases the throughput and yield. An additional advantage is that the increase in viscosity of the reaction mixture as the reaction proceeds is reduced.

Thus according to the present invention there is provided a process for the preparation of an alkyl-, aryl- or alkylaryl- alkoxy ethane sulphonate of general formula:

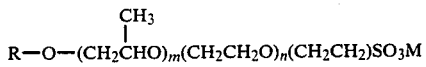

wherein
- R is an alkyl group containing 1 to 24, preferably 8 to 20, carbon atoms or a phenyl group substituted with at least one alkyl group containing 1 to 24, preferably 8 to 20, carbon atoms,
- M is a potassium or ammonium cation,
- m is a number in the range 0 to 5, preferably 0,
- n is a number in the range 1 to 50, preferably 1 to 15, most preferably 4 to 10, and
- the sum of m+n is a number in the range 1 to 50, which process comprises reacting an alkoxy ethane halide of general formula:

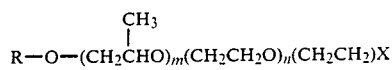

wherein R, m and n are as hereinbefore defined and X is a halide atom, with potassium or ammonium sulphite in the presence of water in amount less than 50% by weight of the alkoxy ethane halide.

"m" and "n" are average values because, during synthesis of the precursor alkoxy alcohol, a range of alkoxylates is formed having a Gaussian distribution. Thus the average values of m and n may be integers or fractions.

It is believed that the reaction can proceed with such a low water content because potassium and ammonium sulphites are more soluble than the corresponding by product halides which tend to salt out as the reaction proceeds. With the more commonly used sodium sulphite, this solubility relationship is reversed, with the result that relatively high water contents are required to maintain the sulphite in solution.

The sulphite is preferably employed in amount 1 to 2, preferably 1 to 1.3 times the stoichiometric quantity.

The water is preferably employed in amount 5 to 40% by weight of the alkoxy ethane halide.

The reaction is suitably carried out at a temperature in the range 80° to 22° C., preferably 140° to 190° C.

The potassium or ammonium sulphite may be used in the pure form or may contain small quantities of other materials such as sodium sulphite.

The reaction is carried out under autogenous pressure. A further advantage of using a lower quantity of water is that the pressure generated during the course of the reaction is therefore reduced.

Copending European patent application No. 0156601 discloses and claims a technique in which a preformed sulphonate is added to the reaction mixture. This procedure can also be employed with benefit in a process according to the present invention.

The sulphonation reaction of the present invention may be carried out in the presence of a diluent which is capable of aiding the separation of water and the reaction products from the reaction mixture.

When the water content is very low, the presence of a diluent is not necessary.

Increasing the water content increases the rate of reaction, but can also increase the viscosity of the reaction mixture and the problems which this entails. In these circumstances it is advantageous to employ a diluent which, inter alia, reduces gel formation. The diluent may be added initially with the reactants or later during the course of the reaction when it is most required. The reactor will generally be fitted with an agitator and it is beneficial to add the diluent as and when required so that the torque on the agitator does not exceed 25 Ncm.

Suitable diluents include $C_1$-$C_{12}$, preferably $C_5$-$C_8$ aliphatic alcohols, especially linear alcohols. Of these, n-hexanol is the most preferred. The presence of an alcohol such as n-hexanol facilitates the stripping of water from the reaction mixture because it forms an azeotrope therewith. Moreover, if a water immiscible alcohol is employed, the azeotrope distillate when cooled to ambient temperature separates into water and alcohol layers thereby facilitating recycle of the alcohol for further use.

The amount of diluent employed will depend upon the reactants used. Generally, the diluent concentration may vary from 2 to 10% w/w, of the total reaction mixture.

In the compounds represented by the formula it is possible to make the ethane sulphonate hydrophobic or hydrophilic by varying the length of the alkyl group and by controlling the average number of the polyoxyalkylene groups, i.e. the value of "n" in the molecule. For instance, ethoxy ethane sulphonates which have an R in which the alkyl groups have more than 12 carbon atoms and an "n" (average) value of less than 5 will be relatively hydrophobic. Ethoxy ethane sulphonates which have an R in which the alkyl groups have less than 12 carbon atoms and an "n" (average) value of more than 5 will be relatively hydrophilic.

Water-soluble ethane sulphonates are more readily prepared than water-insoluble, but the latter may be solubilised by the former. Thus the process may be carried out using a single alkoxy ethane sulphonate to produce a relatively soluble compound, or a mixed feedstock to produce a mixture containing a relatively water-soluble and a relatively water-insoluble compound.

The invention is illustrated with reference to the following Examples of which 1 to 4 and 7 are comparative examples in which the water contents of the reaction mixtures are relatively high and $Na_2SO_3$ or $K_2SO_3$ is used as the sulphonating agent, and 5, 6 and 8 to 11 are embodiments of the invention in which the water contents are relatively low and $K_2SO_3$ is used.

EXAMPLE 1

220 g (0.38 mol) of octadecylphenol (ethoxy)$_4$ ethane chloride, 30.8 g of 84% nonyl phenol (ethoxy)$_7$ ethane sulphonate, 66 g (0.52 mol) of pure sodium sulphite, 330 g of water and 44 g of hexanol were added and heated with vigorous stirring in a pressure tight reactor for 6 hours at 155° C. The initial emulsion turned into a viscous gel during the reaction.

The product was treated with isopropanol which serves a number of functions including breaking the gel, solubilising the surfactant, assisting in azeotroping and precipitating by product salts. The water was then azeotropically distilled off. Dichloromethane was added to complete the precipitation of the inorganic salts which were then removed by filtration. The product was a viscous liquid and was 73% pure (determined by $^{13}C$ NMR, C-$SO_3$Na 50 ppm), the remainder being unreacted ethane chloride, 17% (C-Cl 43 ppm), and initial alcohol, 10% (C-OH 62 ppm).

EXAMPLE 2

220 g (0.38 mol) of octadecylphenol (ethoxy)$_4$ ethane chloride, 30.8 g of 84% nonylphenol (ethoxy)$_7$ethane sulphonate, 95.8 g (0.57 mol) of 94% w/w potassium sulphite, 330 g of water and 44 g of hexanol were added and heated with vigorous stirring in a pressure tight reactor for 6 hours at 155° C. The initial emulsion turned into a viscous gel during the reaction.

The product was treated with isopropanol and the water was azeotropically distilled off. Dichloromethane was added and the inorganic salts were filtered off. The product was a viscous liquid and was 80% pure (determined by $^{13}C$ NMR, C-$SO_3$K 50 ppm), the remainder being unreacted ethane chloride 9% (C-Cl 43 ppm), and initial alcohol 11% (C-OH 62 ppm).

EXAMPLE 3

220 g (0.38 mol) of octadecylphenol (ethoxy)$_4$ ethane chloride, 30.8 g of 84% nonylphenol (ethoxy)$_7$ ethane sulphonate, 71.1 g (0.56 mol) of pure sodium sulphite, 165 g of water and 44 g of hexanol were added and heated with vigorous stirring in a pressure tight reactor for 6 hours at 155° C. The initial emulsion turned into a viscous gel during the reaction.

The product was treated with isopropanol and the water was azeotropically distilled off. Dichloromethane was added and the inorganic salts were filtered off. The product was a viscous liquid and was 67% pure (determined by $^{13}C$ NMR, C-$SO_3$Na 50 ppm), the remainder being unreacted ethane chloride, 24% (C-Cl 43 ppm), and initial alcohol, 9% (C-OH 62 ppm).

EXAMPLE 4

220 g (0.38 mol) of octadecylphenol (ethoxy)$_4$ ethane chloride, 30.8 g of 84% nonylphenol (ethoxy)$_7$ ethane sulphonate, 95.8 g (0.57 mol) of 94% w/w potassium sulphite, 165 g of water and 44 g of hexanol were added and heated with vigorous stirring in a pressure tight reactor for 6 hours at 155° C. The initial emulsion turned into a viscous gel during the reaction.

The product was treated with isopropanol and the water was azeotropically distilled off. Dichloromethane was added and the inorganic salts were filtered off. The product was a viscous liquid and was 86% pure (determined by $^{13}C$ NMR, C-$SO_3$K 50 ppm), the remainder being unreacted ethane chloride, 5% (C-Cl 43 ppm), and initial alcohol, 9% (C-OH 62 ppm).

EXAMPLE 5

330 g (0.57 mol) of octadecylphenol (ethoxy)$_4$ ethane chloride, 46.2 g of 84% nonylphenol (ethoxy)$_7$ ethane sulphonate, 150.6 g (0.85 mol) of 89% w/w potassium sulphite, 66 g of water and 66 g of hexanol were added and heated with vigorous stirring in a pressure tight reactor for 6 hours at 155° C. The reaction mixture remained fluid throughout.

The product was treated with isopropanol and the water was azeotropically distilled off. Dichloromethane was added and the inorganic salts were filtered off. The product was a viscous liquid and was 98% pure (determined by $^{13}C$ NMR, C-$SO_3$K 50 ppm), the remainder being the unreacted ethane chloride, 3% (C-Cl 43 ppm), and the initial alcohol 8%, (C-OH 62 ppm).

EXAMPLE 6

229 g (0.42 mol) of octadecylphenol-(ethoxy)$_3$-ethane chloride and 190 g (0.32 mol) of nonylphenol-(ethoxy)$_7$-ethane chloride, together with 56 g of a 1.3:1 molar mixture of the sulphonates corresponding to these chlorides, 146 g (0.82 mol) of 89% w/w potassium sulphite and 42 g of water were added and heated with vigorous stirring in a pressure tight reactor for 6 hours at 160° C. The reaction mixture remained fluid throughout.

The product was treated with isopropanol and the water was azeotropically distilled off. Dichloromethane was added and the inorganic salts were filtered off. The product was a viscous liquid and was 86% pure (determined by $^{13}C$ NMR, C-$SO_3$K 50 ppm), the remainder being the unreacted ethane chloride, 7%(C-Cl 43 ppm), and the initial alcohol, 7%(C-OH 62 ppm).

EXAMPLE 7

136 g (0.25 mol) of octadecylphenol-(ethoxy)$_3$-ethane chloride and 138 g (0.23 mol) of nonylphenol-(ethoxy)$_7$-ethane chloride, together with 42 g of a 1.25:1 molar mixture of the sulphonates corresponding to these chlorides, 79 g (0.63 mol) of pure sodium sulphite and 274 g of water were added and heated with vigorous stirring in a pressure tight reactor for 8 hours at 180° C. The reaction mixture remained fluid throughout.

The product was treated with isopropanol and the water was azeotropically distilled off. More isopropanol was added and the inorganic salts were filtered off. The product was a viscous liquid and was 85% pure (determined by $^{13}$C NMR, C-SO$_3$Na 50 ppm), the remainder being the initial alcohol, 15% (C-OH 62 ppm).

EXAMPLE 8

136 g (0.25 mol) of octadecylphenol-(ethoxy)$_3$-ethane chloride and 138 g (0.23 mol) of nonylphenol-(ethoxy)$_7$-ethane chloride, together with 42 g of a 1.25:1 molar mixture of the sulphonates corresponding to these chlorides, 88 g (0.53 mol) of 96% w/w potassium sulphite and 103 g of water were added and heated with vigorous stirring in a pressure tight reactor for 4 hours at 180° C. Hexanol was added to the reaction mixture in 10 ml portions after 15, 20 and 38 minutes to prevent gel formation.

The product was treated with isopropanol and the water was azeotropically distilled off. More isopropanol was added and the inorganic salts were filtered off. The product was a viscous liquid and was 86% pure (determined by $^{13}$C NMR, C-SO$_3$K 50 ppm), the remainder being the initial alcohol, 14% (C-OH 62 ppm).

EXAMPLE 9

130 g (0.24 mol) of octadecylphenol-(ethoxy)$_3$-ethane chloride and 131 g (0.22 mol) of nonylphenol-(ethoxy)$_7$-ethane chloride, together with 41 g of a 1.25:1 molar ratio of the sulphonates corresponding to these chlorides, 84 g (0.51 mol) of 96% w/w potassium sulphite and 99 g of water were added and heated with vigorous stirring in a pressure tight reactor for 2 hours at 180° C. Hexanol was added as required throughout the duration of the reaction to maintain a torque between 17 and 20 Ncm measured on the agitator in the vessel. The final hexanol content of the reaction mixture was 4.1%.

The product was treated with isopropanol and the water was azeotropically distilled off. More isopropanol was added and the inorganic salts were filtered off. The product was a viscous liquid and was 91% pure (determined by $^{13}$C NMR, C-SO$_3$K 50 ppm), the remainder being the initial alcohol, 9% (C-OH 62 ppm).

EXAMPLE 10

136 g (0.25 mol) of octadecylphenol-(ethoxy)$_3$-ethane chloride and 138 g (0.23 mol) of nonylphenol-(ethoxy)$_7$-ethane chloride, together with 42 g of a 1.25:1 molar ratio of the sulphonates corresponding to these chlorides, 88 g (0.53 mol) of 96% w/w potassium sulphite and 69 g of water were added and heated with vigorous stirring in a pressure tight reactor for 2 hours at 180° C. Hexanol was added as required throughout the duration of the reaction to maintain a torque of between 19 and 21 Ncm. The final hexanol content of the reaction mixture was 3.5%.

The product was treated with isopropanol and the water was azeotropically distilled off. More isopropanol was added and the inorganic salts were filtered off. The product was a viscous liquid and was 87% pure (determined by $^{13}$C NMR, C-SO$_3$K 50 ppm), the remainder being the initial alcohol, 13% (C-OH 62 ppm).

EXAMPLE 11

168 g (0.31 mol) of octadecylphenol-(ethoxy)$_3$-ethane chloride and 170 g (0.29 mol) of nonylphenol-(ethoxy)$_7$-ethane chloride, together with 14 g of a 0.93:1 molar mixture of the sulphonates corresponding to these chlorides, 109 g (0.66 mol) of 96% w/w potassium sulphite and 34 g of water were added and heated with vigorous stirring in a pressure tight reactor for 2.25 hours. The reaction mixture remained fluid throughout.

The product was treated with isopropanol and the water was azeotropically distilled off. More isopropanol was added and the inorganic salts were filtered off. The product was a viscous liquid and was 84% pure (determined by $^{13}$C NMR, C-SO$_3$K 50 ppm), the remainder being unreacted ethane chloride, 3% (C-Cl 43 ppm) and the initial alcohol, 13% (C-OH 62 ppm).

The significant features of Examples 1 to 6 may be summarised as follows:

| Ex | Sulphonating Agent | Water Content (% by wt of ethane halide) | Diluent Present | Reaction Gelled | Product Purity % |
|---|---|---|---|---|---|
| 1 | Na$_2$SO$_3$ | 150 | Yes | Yes | 73 |
| 2 | K$_2$SO$_3$ | 150 | Yes | Yes | 80 |
| 3 | Na$_2$SO$_3$ | 75 | Yes | Yes | 67 |
| 4 | K$_2$SO$_3$ | 75 | Yes | Yes | 86 |
| 5 | K$_2$SO$_3$ | 20 | Yes | No | 89 |
| 6 | K$_2$SO$_3$ | 10 | No | No | 86 |

Example 1 shows that the use of sodium sulphite in the presence of a large quantity of water, despite the addition of a diluent, results in gelling of the reaction mixture and a product of low purity.

Whilst a refined product may be extracted from a gelled reaction mixture in the laboratory, such a procedure would not be desirable on an industrial scale.

Example 2 shows that replacing the sodium sulphite by potassium sulphite results in a product of increased purity, but gelling problems still remain because of the high water content of the reaction mixture.

Example 3 reverts to sodium sulphite and reduces the water content to half its previous value, but still above the level of the present invention. Gelling problems remain and the purity of the product is reduced when compared with Example 1.

Example 4 utilises potassium sulphite and the water content is reduced to the level of Example 3. In this example the purity of the product is increased when compared with Example 2, although the reaction mixture continues to gel.

Example 5 continues with potassium sulphite and reduces the water content to 20% by weight of the halide. The product purity continues to improve and the reaction mixture no longer gels.

In Example 6 a mixed feedstock giving rise to a hydrophobic/hydrophilic product was employed and the water content was reduced still further to 10% by weight of the mixed halides.

The significant features of Examples 7 to 11 may be summarised as follows:

| Ex | Sulpho-nating Agent | Water Content (% by wt of ethane halide) | Diluent Present | Reaction Time (hrs) | Reaction Gelled | Product Purity % |
|---|---|---|---|---|---|---|
| 7 | Na$_2$SO$_3$ | 100 | No | 8 | No | 85 |
| 8 | K$_2$SO$_3$ | 38 | Yes | 4 | No | 86 |
| 9 | K$_2$SO$_3$ | 38 | Yes | 2 | No | 91 |
| 10 | K$_2$SO$_3$ | 25 | Yes | 2 | No | 87 |
| 11 | K$_2$SO$_3$ | 10 | No | 2¼ | No | 84 |

In Examples 7 to 11, the reactions were taken to completion by analysing samples at regular intervals.

These examples show how the reaction time is reduced by reducing the water content of the reaction mixture. Compare Example 7 with Examples 8 to 11.

In Example 8, the diluent was added incrementally on a time basis. In Example 9, the diluent was added as required in order to keep the torque on the stirrer at a low value. A comparison of these examples shows that the latter is the more effective technique.

In Example 9 the water content is that required to dissolve the K$_2$SO$_3$ at 20° C., in Example 10, that required at 100° C.

Example 11 employs a particularly low water content and is able to avoid the use of a diluent.

We claim:

1. A process for the preparation of an alkyl-, aryl- or alkylaryl-alkoxy ethane sulphonate of general formula:

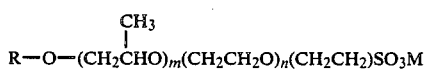

wherein
R is an alkyl group containing 1 to 24 carbon atoms or a phenyl group substituted with at least one alkyl group containing 1 to 24 carbon atoms,
M is a potassium or ammonium cation,
m is a number in the range 0 to 5,
n is a number in the range 1 to 50, and the sum of m+n is a number in the range 1 to 50,
which process comprises reacting an alkoxy ethane halide of general formula:

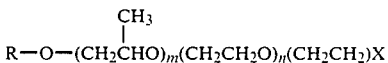

wherein R, m and n are as hereinbefore defined and X is a halide atom, with potassium or ammonium sulphite in the presence of water wherein the water is present in amount less than 50% by weight of the alkoxy ethane halide.

2. A process according to claim 1 wherein R is a phenyl group substituted with an alkyl group containing 8 to 20 carbon atoms,
M is a potassium cation,
m is 0, and
n is a number in the range 1 to 15.

3. A process according to claim 1 wherein the sulphite is employed in an amount in the range stoichiometric to twice the stoichiometric quantity.

4. A process according to claim 1 wherein the water is employed in amount 5 to 40% by weight of the alkoxy ethane halide.

5. A process according to claim 1 wherein the reaction is carried out at a temperature in the range 80° to 220° C.

6. A process according to claim 1 wherein the reaction is carried out in the presence of a preformed sulphonate.

7. A process according to claim 1 wherein the reaction is carried out in the presence of a diluent.

8. A process according to claim 7 wherein the diluent is an aliphatic alcohol containing 1 to 12 carbon atoms per molecule.

9. A process according to claim 7 wherein the reactor for the process contains an agitator and the diluent is added as and when required so that the torque on the agitator does not exceed 25 Ncm.

10. A process according to claim 1 wherein the feedstock is a mixed feedstock containing (a) an ethoxy ethane halide capable of forming a relatively hydrophobic sulphonate and (b) an ethoxy ethane halide capable of forming a relatively hydrophilic sulphonate, compound (a) containing a phenyl group substituted with an alkyl group containing at least 12 carbon atoms and having less than 5 ethoxy groups per molecule, compound (b) containing a phenyl group substituted with an alkyl group containing less than 12 carbon atoms and more than 5 ethoxy groups per molecule.

* * * * *